US010521578B2

(12) United States Patent
Higuchi

(10) Patent No.: US 10,521,578 B2
(45) Date of Patent: *Dec. 31, 2019

(54) AUTHENTICATION USING PRISM MEMBER

(71) Applicant: NEC Corporation, Minato-ku, Tokyo (JP)

(72) Inventor: Teruyuki Higuchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,057

(22) Filed: Sep. 6, 2018

(65) Prior Publication Data

US 2019/0005221 A1    Jan. 3, 2019

Related U.S. Application Data

(63) Continuation of application No. 14/763,876, filed as application No. PCT/JP2014/051647 on Jan. 27, 2014, now Pat. No. 10,229,257.

(51) Int. Cl.
*G06F 21/32* (2013.01)
*A61B 5/00* (2006.01)
(Continued)

(52) U.S. Cl.
CPC ............ *G06F 21/32* (2013.01); *A61B 5/0077* (2013.01); *A61B 5/1172* (2013.01); *G06K 9/00046* (2013.01)

(58) Field of Classification Search
CPC ............... A61B 5/1172; G02B 5/0808; G06K 2009/0006; G06K 9/00013; G06K 9/00006; G06K 9/00046
See application file for complete search history.

(56) References Cited

U.S. PATENT DOCUMENTS 5,077,803 A * 12/1991 Kato .................. A61B 5/1172
356/71
5,177,802 A * 1/1993 Fujimoto ............. A61B 5/1172
356/71
(Continued)

FOREIGN PATENT DOCUMENTS

JP    2003085538 A    3/2003
JP    2006065400 A    3/2006
(Continued)

OTHER PUBLICATIONS

International Search Report for PCT Application No. PCT/JP2014/051647, dated Apr. 8, 2014.
(Continued)

*Primary Examiner* — Hai Phan
*Assistant Examiner* — Son M Tang

(57) ABSTRACT

A prism member of an authentication apparatus includes a living body contact surface in contact with a visible light-radiated living body, and an imaging surface opposed to the living body contact surface and formed at a position in generally parallel therewith. The prism member includes a reflection surface in contact with the living body contact surface and the imaging surface, and to totally reflect light reflected off from the living body contact surface toward the imaging surface. The reflection surface is at an angle such that light from an inside of the prism member is totally reflected at the living body contact surface in an optical path running from the imaging surface and reaching the living body contact surface via the reflection surface. A first imaging unit captures an image including at least a part of said body contact surface and at least a part of the reflection surface.

15 Claims, 10 Drawing Sheets

(51) Int. Cl.
*A61B 5/1172* (2016.01)
*G06K 9/00* (2006.01)

(56) References Cited

U.S. PATENT DOCUMENTS

| | | | | |
|---|---|---|---|---|
| 5,448,649 A * | 9/1995 | Chen | ............... | G06K 9/00046 356/71 |
| 5,619,586 A * | 4/1997 | Sibbald | ............... | G06K 9/00046 356/71 |
| 5,650,842 A * | 7/1997 | Maase | ............... | G06K 9/00046 356/71 |
| 6,127,674 A * | 10/2000 | Shinzaki | ............... | G06K 9/00046 250/227.28 |
| 6,259,108 B1 * | 7/2001 | Antonelli | ............... | G06K 9/00026 250/556 |
| 6,381,347 B1 * | 4/2002 | Teng | ............... | G06K 9/00046 356/71 |
| 6,954,261 B2 * | 10/2005 | McClurg | ............... | G06K 9/00046 356/71 |
| 6,956,608 B1 * | 10/2005 | Shapiro | ............... | G06K 9/00046 250/227.28 |
| 7,689,013 B2 * | 3/2010 | Shinzaki | ............... | G06K 9/0012 340/5.52 |
| 7,747,046 B2 * | 6/2010 | McClurg | ............... | G06K 9/00046 382/124 |
| 8,811,682 B2 * | 8/2014 | Kanda | ............... | G06K 9/00046 340/5.83 |
| 8,854,179 B2 * | 10/2014 | Argudyaev | ............... | G06K 9/00053 340/5.52 |
| 9,619,690 B2 * | 4/2017 | Higuchi | ............... | A61B 5/1171 |
| 2003/0021450 A1 * | 1/2003 | Shapiro | ............... | G06K 9/00046 382/124 |
| 2003/0169910 A1 * | 9/2003 | Reisman | ............... | G06K 9/00087 382/124 |
| 2005/0249390 A1 * | 11/2005 | McClurg | ............... | G06K 9/00046 382/127 |
| 2006/0177107 A1 * | 8/2006 | Ishii | ............... | G06K 9/00026 382/115 |
| 2007/0014437 A1 * | 1/2007 | Sato | ............... | G06K 9/00013 382/115 |
| 2007/0116331 A1 * | 5/2007 | Rowe | ............... | G06K 9/00046 382/127 |
| 2007/0280514 A1 * | 12/2007 | Heidt | ............... | G06K 9/00046 382/124 |
| 2008/0152196 A1 * | 6/2008 | Saliba | ............... | G06K 9/00046 382/115 |
| 2008/0273771 A1 * | 11/2008 | Hsieh | ............... | G06K 9/00046 382/127 |
| 2009/0067687 A1 * | 3/2009 | Boshra | ............... | G06F 21/32 382/124 |
| 2009/0214083 A1 * | 8/2009 | Sato | ............... | A61B 5/117 382/107 |
| 2010/0168585 A1 * | 7/2010 | Fujii | ............... | A61B 5/0261 600/476 |
| 2010/0321152 A1 * | 12/2010 | Argudyaev | ............... | G06K 9/00046 340/5.53 |
| 2011/0007951 A1 * | 1/2011 | Mil'shtein | ............... | G06K 9/00033 382/124 |
| 2013/0136327 A1 * | 5/2013 | Kamei | ............... | A61B 5/117 382/128 |
| 2014/0023249 A1 | 1/2014 | Higuchi | | |
| 2014/0286548 A1 * | 9/2014 | Shin | ............... | G06K 9/00114 382/127 |
| 2015/0054932 A1 * | 2/2015 | Higuchi | ............... | A61B 5/1171 348/77 |
| 2015/0062319 A1 * | 3/2015 | Higuchi | ............... | A61B 5/1171 348/77 |
| 2015/0117726 A1 * | 4/2015 | Higuchi | ............... | A61B 5/1171 382/124 |
| 2016/0070896 A1 * | 3/2016 | Higuchi | ............... | A61B 5/0077 340/5.83 |
| 2017/0032176 A1 * | 2/2017 | Higuchi | ............... | A61B 5/0077 |

FOREIGN PATENT DOCUMENTS

| | | |
|---|---|---|
| JP | 2010503079 A | 1/2010 |
| JP | 2010134877 A | 6/2010 |
| TW | 201145179 A | 12/2011 |
| TW | 201224953 A | 6/2012 |
| WO | 2012/133110 A1 | 10/2012 |
| WO | 2013/146759 A1 | 10/2013 |
| WO | 2013/146760 A1 | 10/2013 |
| WO | 2013/146761 A1 | 10/2013 |

OTHER PUBLICATIONS

Taiwanese Office Action for TW Application No. 103103443 dated Jul. 30, 2015 with English Translation.
Japanese Office Action for JP Application No. 2014-559663 dated Sep. 16, 2016.
U.S. Office Action for U.S. Appl. No. 14/763,876 dated Oct. 31, 2018.
U.S. Office Action for U.S. Appl. No. 16/123,008 dated May 16, 2019.

* cited by examiner

AUTHENTICATION USING PRISM MEMBER

CROSS-REFERENCE TO RELATED APPLICATIONS

The present application is a continuation application of U.S. patent application Ser. No. 14/763,876 filed on Nov. 17, 2015, which is a National Stage Entry of International Application PCT/JP2014/051647, filed on Jan. 27, 2014, which claims the benefit of priority from Japanese Patent Application 2013-016746, filed on Jan. 31, 2013, the disclosures of all of which are incorporated herein, in their entirety, by this reference.

TECHNICAL FIELD

The present invention relates to an authentication apparatus, a prism member for authentication, and an authentication method.

BACKGROUND ART

Commonly used living body authentication apparatuses using fingerprints, which are a kind of living body feature, to authenticate individuals employ a method using a critical angle of total reflection by a triangular (optical) prism (for example, see Patent literature 1). The method involves reading bumpiness (ridges and furrows) of a skin surface, which enables a fingerprint image to be easily obtained with high contrast. The method has thus highly compatible with "fingerprinting" wherein fingerprints are collected by impressing an inked fingertip against paper, and the method has been used in judicial and police purposes.

On the other hand, there are recently increasing criminal acts, including use of a fake finger fabricated from resin such as silicone, and "identity theft" by attaching a semitransparent bumpy film imitating fingerprints to a real fingertip to pretend to be someone else. Detection of such an act may involve acquiring a high-contrast image having high contrast for matching fingerprints or the like, and in addition, a natural image of fingers that is similar to visual observation for detecting a counterfeit, and visually verifying these images.

Accordingly, there has been proposed an authentication apparatus using a contactless method in which fingers do not touch a prism, and acquiring a fingerprint image similar to natural visualization by naked eyes to achieve authentication (for example, see Patent literature 2).

CITATION LIST

Patent Literature

[Patent Literature 1]
U.S. Pat. No. 6,381,347
[Patent Literature 2]
Japanese Unexamined Patent Application Publication No. 2003-085538

SUMMARY OF INVENTION

Technical Problem

A lot of databases have been produced of impressed fingerprints using a conventional prism, and compatibility is extensively required in images by the authentication apparatuses from the viewpoint of inheritability. Moreover, advantages of images of impressed fingerprints include easy matching with leftover fingerprints. The leftover fingerprints are residual fingerprints left behind in a criminal scene or the like, which may sometimes serve as a definitive factor for criminal investigation, and are also useful as judicial evidence.

However, when fingerprints are captured without pressing fingers against glass as in the contactless method, the degree of deformation of the fingers is different between the state in which they are unpressed against glass and that in which they are pressed against glass because of flexibility of the fingers, and accordingly, a fingerprint image based on the contactless method differs from that based on the contact method.

Therefore, there is a problem that an image of fingerprints or the like obtained based on the contactless method is incompatible with impressed fingerprints using a conventional prism. Moreover, since fingerprint imaging based on the contactless method results in low contrast, it is unsuitable for an identification method based on observation of an image by naked eyes in judicial use, etc.

On the other hand, to prevent criminal acts, including use of a fake finger fabricated from resin such as silicone, and "identity theft" by attaching a semitransparent bumpy film imitating fingerprints to a real fingertip to pretend to be someone else, acquisition of a natural image of fingers is required during matching at matching worksites.

The present invention has been made in view of such problems, and its object is to provide an authentication apparatus, a prism member for authentication, and an authentication method enabling simultaneous acquisition of a high-contrast image with contrast sufficient for matching in a state in which a living body is in contact with a prism and a natural image of the living body similar to visual observation by an imaging apparatus.

Solution to Problem

The present invention is an authentication apparatus including a prism member, a first imaging unit, and a visible light source configured to radiate a visible light to a living body, wherein said prism member comprises: a living body contact surface configured to be in contact with the living body; an imaging surface configured to be opposed to said living body contact surface and be formed at a position in generally parallel therewith; and a reflection surface configured to be in contact with said living body contact surface and said imaging surface, and to totally reflect light reflected off from said living body contact surface toward said imaging surface, wherein said reflection surface is disposed at such an angle that light from an inside of said prism member is totally reflected at said living body contact surface in an optical path running from said imaging surface and reaching said living body contact surface by way of said reflection surface, and said first imaging unit captures a living-body reflected light that is light radiated from said visible light source reflected off by the living body in contact with said living body contact surface, and a reflection surface reflected light that is said living-body reflected light reflected off by said reflection surface.

The present invention is a prism member for authentication of a living body, comprising: a living body contact surface configured to be in contact with a living body; an imaging surface configured to be opposed to said living body contact surface and be formed at a position in generally parallel therewith; and a reflection surface configured to be in contact with said living body contact surface and said imaging surface, and to totally reflect light reflected off from said living body contact surface toward said imaging surface, wherein said reflection surface is disposed at such an angle that light from an inside of said prism member is totally reflected at said living body contact surface in an optical path running from said imaging surface and reaching said living body contact surface by way of said reflection surface.

The present invention is an authentication method, in a prism member comprising:

a living body contact surface configured to be in contact with a living body; an imaging surface configured to be opposed to said living body contact surface and be formed at a position in generally parallel therewith; and a reflection surface configured to be in contact with said living body contact surface and said imaging surface, and to totally reflect light reflected off from said living body contact surface toward said imaging surface, wherein said reflection surface is disposed at such an angle that light from an inside of said prism member is totally reflected at said living body contact surface in an optical path running from said imaging surface and reaching said living body contact surface by way of said reflection surface, said method comprising: bringing a living body into contact with said living body contact surface of said prism member; radiating a visible light to said living body; and imaging a living-body reflected light that is light radiated from said visible light source and transmitted through said imaging surface reflected off by the living body in contact with said living body contact surface, and a reflection surface reflected light that is said living-body reflected light reflected off by said reflection surface.

Advantageous Effect of Invention

According to the present invention, a high-contrast image with contrast sufficient for matching in a state in which a living body is in contact with a prism and a natural image of the living body similar to visual observation may be simultaneously acquired by one imaging apparatus.

DESCRIPTION OF EMBODIMENTS

Now embodiments of the present invention will be described in detail.

First, the principle of a prism in accordance with the present invention will be described.

Figure 1:
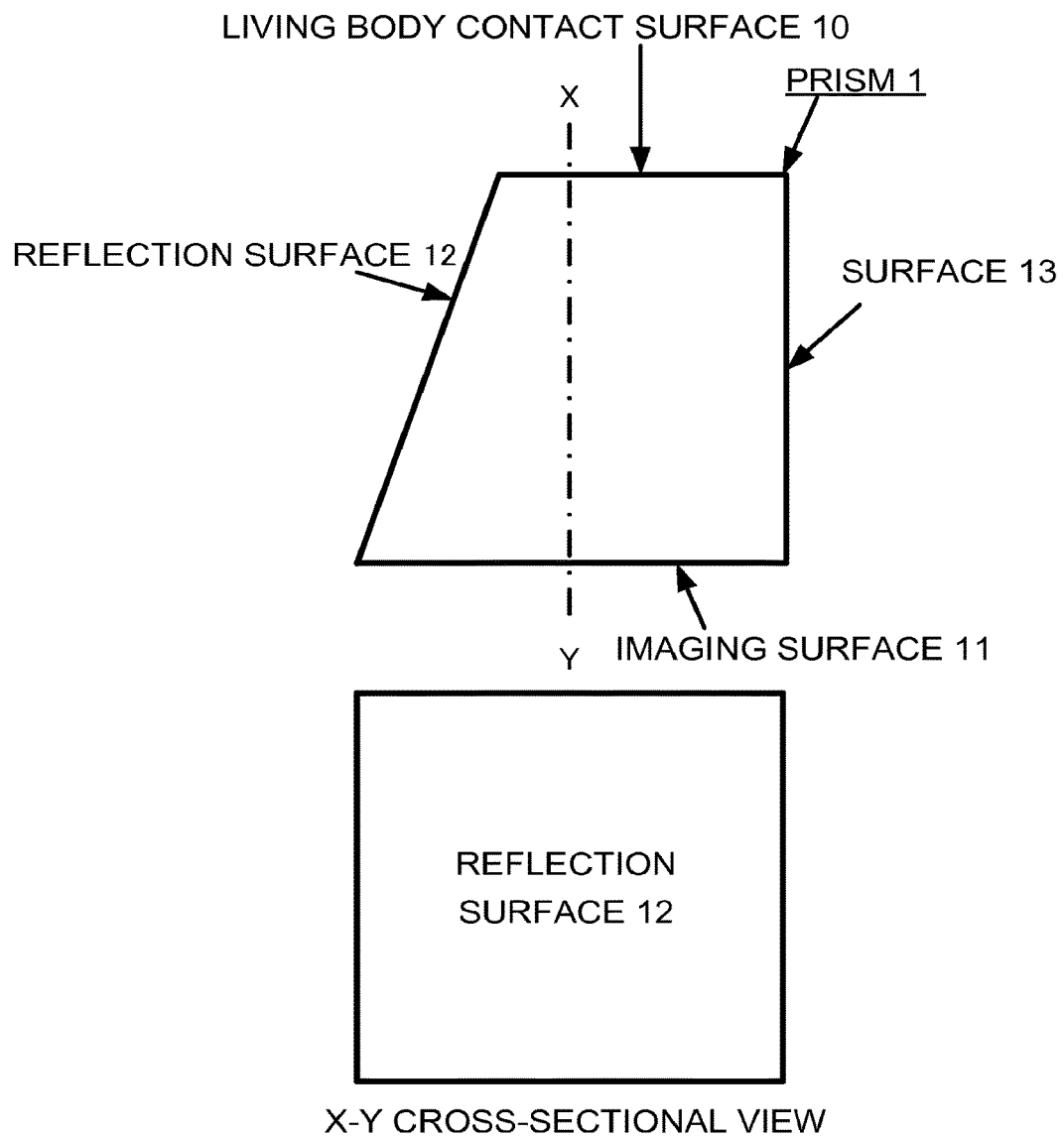
FIG. 1 is a diagram showing a configuration of a prism 1 in accordance with the present invention.

FIG. 1 is a diagram showing a configuration of a prism 1 having a modified trapezoidal shape in accordance with the present invention. In FIG. 1, reference numeral 10 designates a living body contact surface brought into contact with a living body (for example, a finger), 11 designates an imaging surface which is formed in generally parallel with the living body contact surface 10 on the side on which an imaging apparatus such as a camera is disposed, 12 designates a reflection surface formed contiguous with the living body contact surface 10 and imaging surface 11, and 13 designates a surface facing the reflection surface 12.

The reflection surface 12 is disposed at such an angle that light from the inside of the prism 1 is totally reflected at the living body contact surface 10 in an optical path running from the imaging surface 11 and reaching the living body contact surface 10 by way of the reflection surface 12. In other words, it is disposed at such an angle that, due to the difference in refractive index between the air layer and prism main body, light penetrating into the prism main body from the living body contact surface 10 via the air layer does not reach the reflection surface, and at the same time, light reflected off from the living body contact surface 10 is totally reflected toward the imaging surface 11.

Next, each optical path will be described with reference to FIGS. 2 to 5. While the following description addresses a case in which the living body is a finger 2, the present invention is not limited thereto. For example, it may be applied to palmprint authentication. Moreover, the present embodiment addresses a case in which a visible light source 3 is disposed on the side of the lower surface of the prism 1 so that the radiated light reflected by furrows and ridges of the finger 2 put against the living body contact surface 10 is captured by an imaging apparatus 4 disposed below the imaging surface 11.

Light radiated from the visible light source 3 is reflected by furrows and ridges of the finger 2 put against the living body contact surface 10.

Figure 2:
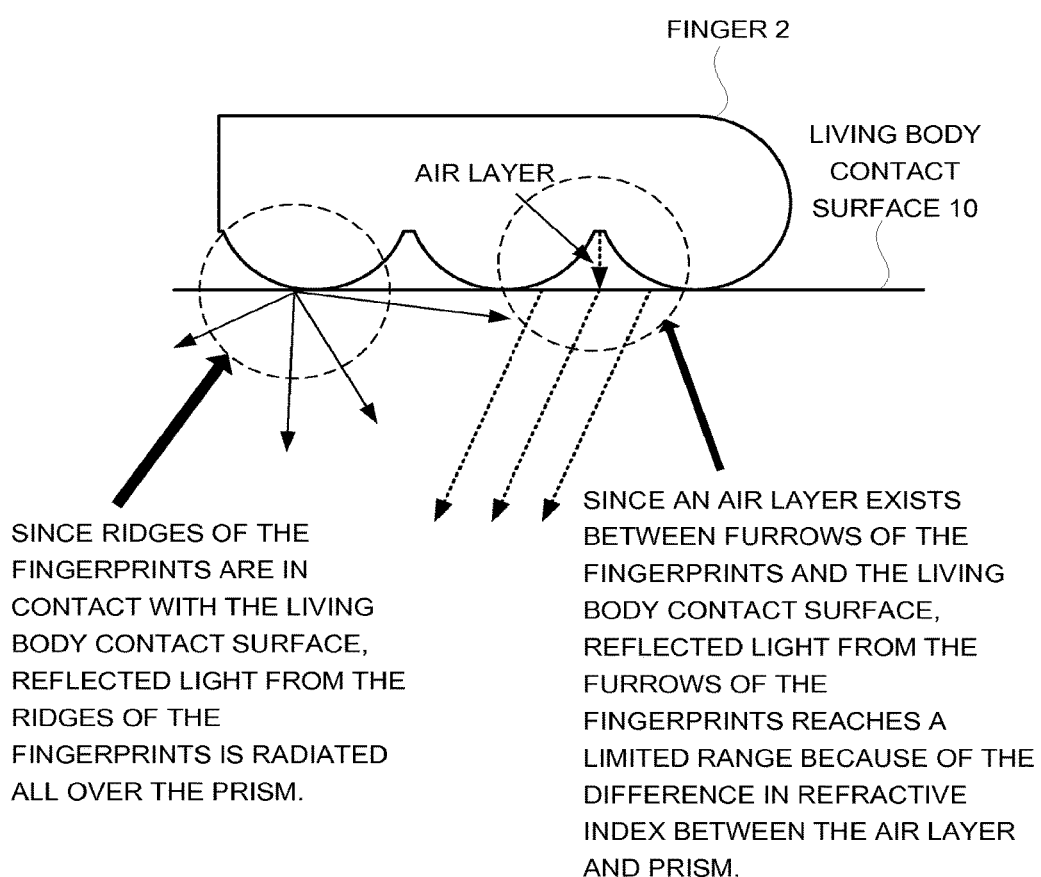
FIG. 2 is a diagram for explaining the prism 1 in accordance with the present invention.

In this condition, as shown in FIG. 2, ridges of the finger 2 are in contact with the living body contact surface 10, and therefore, the refractive index of light reflected by ridges of the finger 2 is approximately the same as that of the prism 1 (glass). Hence, the light reflected by ridges of the finger 2 may be considered similarly to light reflected at the living body contact surface 10, wherein the light is radiated in almost all directions in the inside of the prism 1 and can reach the whole region below the living body contact surface 10.

Figure 3:
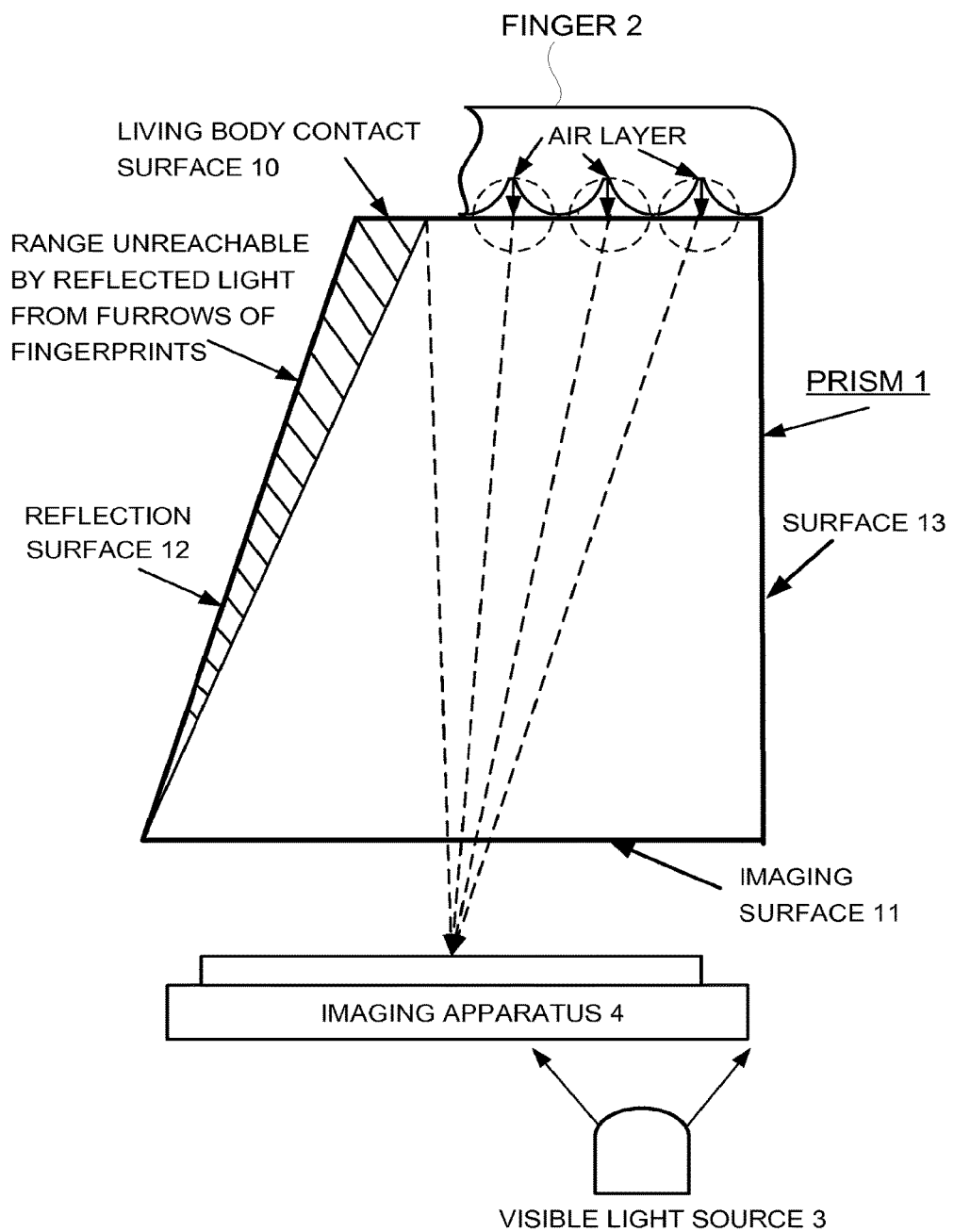
FIG. 3 is a diagram for explaining the prism 1 in accordance with the present invention.

On the other hand, furrows of the finger 2 are not in contact with the living body contact surface 10, creating an air layer between the furrows of the finger 2 and the living body contact surface 10. Therefore, a reflected light from the furrows of the finger 2 passes through the living body contact surface 10 via the air layer. Since the refractive index, however, is different between the air having a refractive index of 1.0, glass having a refractive index of 1.3 to 1.5, and moisture and skin having a refractive index of 1.3 to 1.4, the reflected light from the furrows of the finger 2 causes a refractive phenomenon different from that by the reflected light from ridges of the finger 2, so that the reflected light from the furrows does not radiate in all directions and does not reach a certain range in the inside of the prism 1. The reflection surface 12 here is disposed at such an angle that light from the inside of the prism 1 is totally reflected at the living body contact surface 10 in an optical path running from the imaging surface 11 and reaching the living body contact surface 10 by way of the reflection surface 12. In other words, the reflection surface 12 is disposed in a range unreachable by light transmitted through the living body contact surface 10 from the air layer and penetrating into the prism 1, and at the same time, disposed at such an angle that light reflected off from the living body contact surface 10 is totally reflected toward the imaging surface 11. Therefore, as shown in FIG. 3, a light reflected at the furrows of the finger 2 and transmitted through the living body contact surface 10 via the air layer does not reach the reflection surface 12, so that there is no reflected light from the furrows passing from the living body contact surface 10 and reaching the imaging surface 11 by way of the reflection surface 12, leaving only a reflected light passing from the living body contact surface 10 and directly reaching the imaging surface 11 alone.

Figure 4:
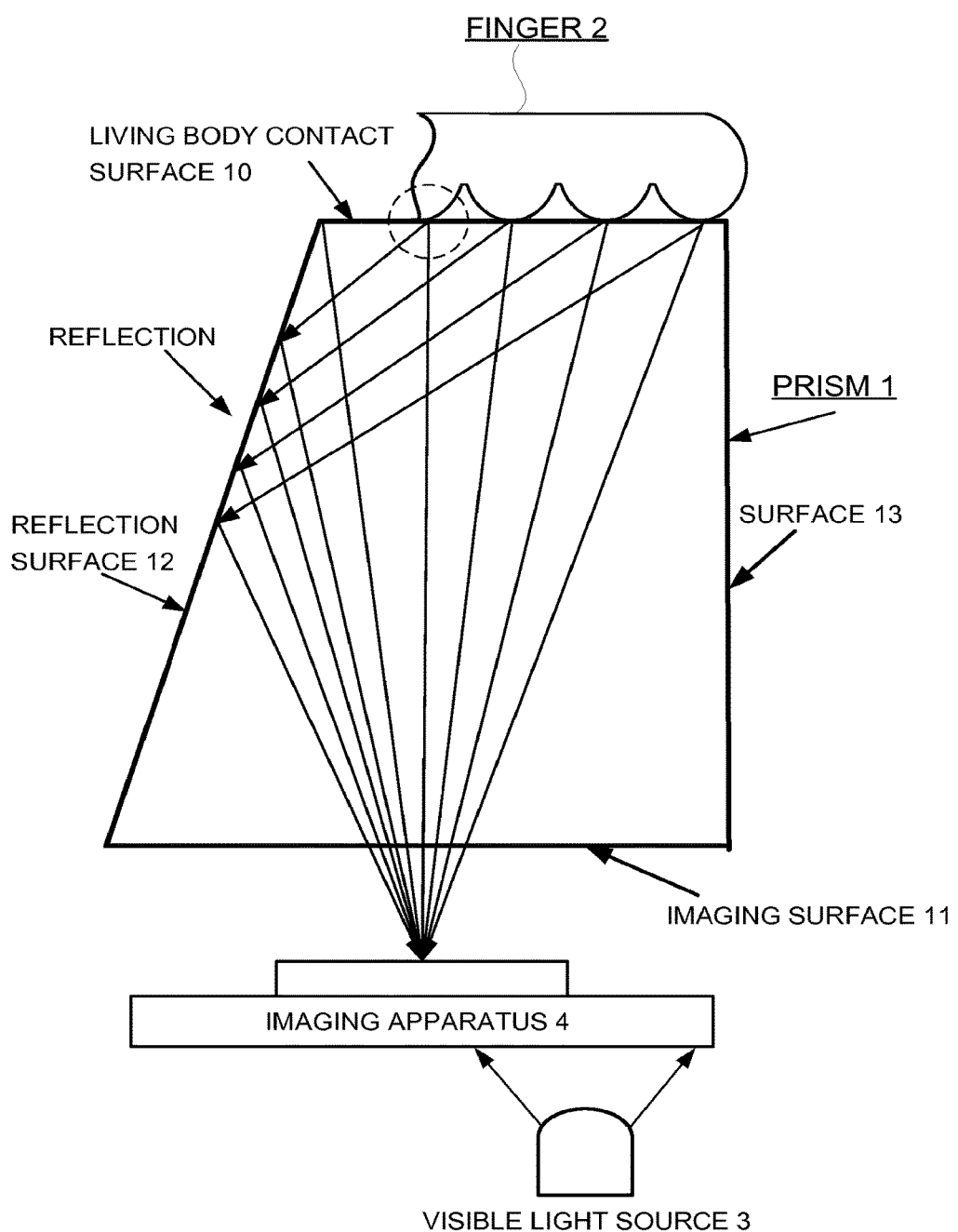
FIG. 4 is a diagram for explaining the prism 1 in accordance with the present invention.

Next, as for the optical paths for the ridges of the finger 2, light reflected by the ridges of the finger 2 is radiated in almost all directions in the inside of the prism 1 and can reach the whole region below the living body contact surface 10 as described above; as such, the optical paths include those of light directly reaching the imaging surface 11 and those of light reflected by the reflection surface 12 and reaching the imaging surface 11, as shown in FIG. 4.

Figure 5:
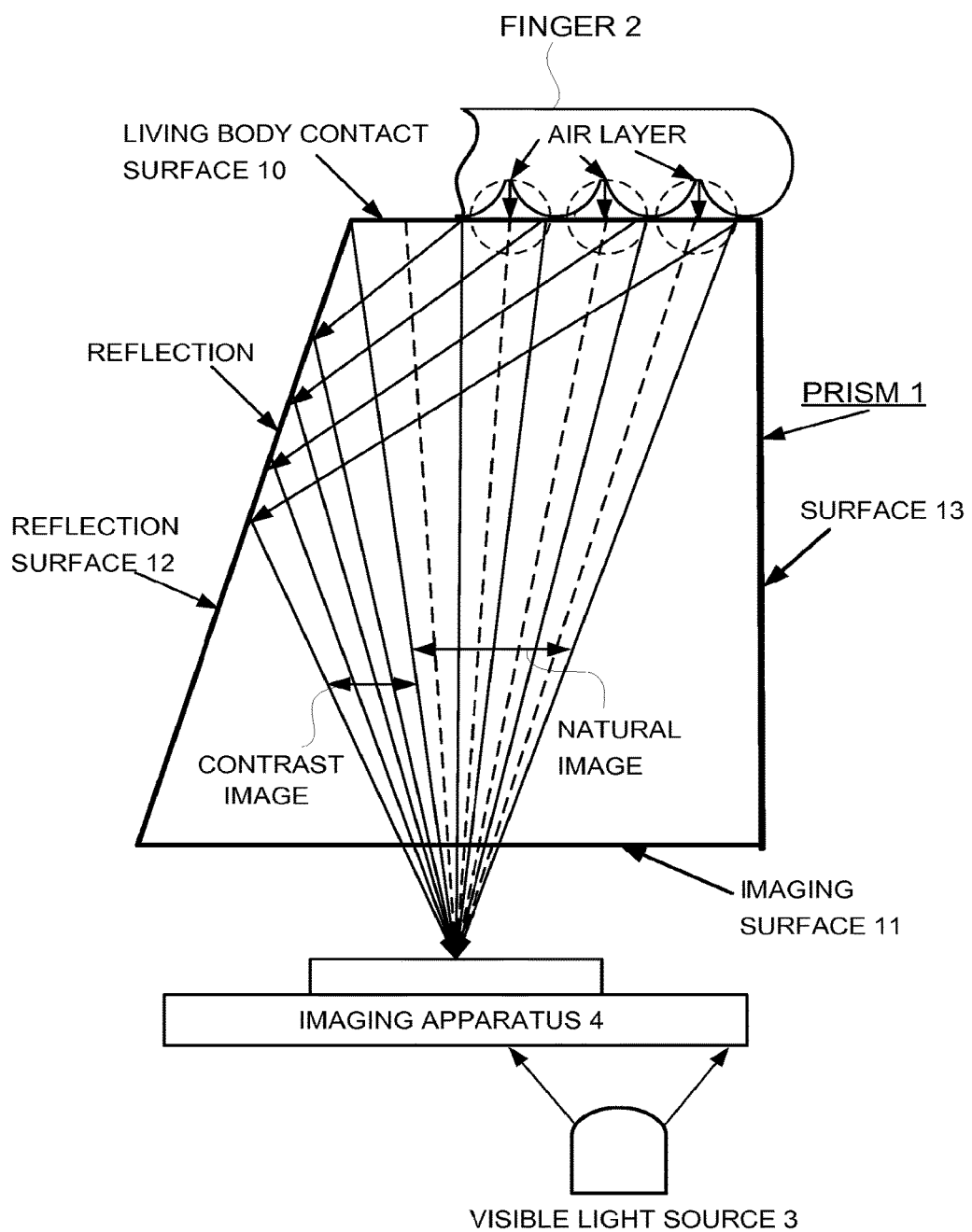
FIG. 5 is a diagram for explaining the prism 1 in accordance with the present invention.

Since the imaging apparatus 4 captures light transmitted through the imaging surface 11, as shown in FIG. 5, two kinds of images transmitted through the imaging surface 11 are captured. One of them is an image for optical paths of a reflected light from the ridges of the finger 2 passing from the living body contact surface 10 and reaching the imaging surface 11 by way of the reflection surface 12. Since the image is by only a reflected light from the ridges of the finger 2, it is a fingerprint image with high contrast (referred to as high-contrast image hereinbelow) having dark furrows of the finger 2 and bright ridges of the finger 2. The other one is an image for optical paths of part of the reflected light reflected by the furrows and ridges of the finger 2 put against the living body contact surface 10 that directly reaches the imaging surface 11. Since the image is similar to that of the finger 2 put against the living body contact surface 10 as directly viewed from imaging surface 11, the image captured by the imaging apparatus 4 is a natural image of the finger 2 (referred to as natural image hereinbelow).

By using the prism 1 as described above in the authentication apparatus, the imaging apparatus 4 can capture a high-contrast image and a natural image in one shot of imaging, as shown in FIG. 5.

Since it is sufficient for the natural image to allow judgment as to whether the fingerprints are fake or genuine, acquisition of a wide-area image is not necessary. Rather, it is more desirable to analyze an enlarged image in detail. In the imaging of the finger 2 using the prism 1 according to the present embodiment, the optical path for obtaining a natural image is a path running from the living body contact surface 10 and directly reaching the imaging surface 11, which is the shortest optical path, and therefore, a natural image enlarged enough to detect counterfeits can be obtained.

On the other hand, since the high-contrast image is used in fingerprint matching, it is more desirable to acquire a fingerprint image in a wider area so that many feature points are present. To acquire a fingerprint image in a wider area, it is necessary to lengthen the optical path from the living body contact surface 10 to the imaging surface 11. In the imaging of the finger 2 using the prism 1 according to the present embodiment, the optical path for obtaining a high-contrast image is a path running from the living body contact surface 10 to the imaging surface 11 by way of the reflection surface 12, and therefore, the optical path is long enough to capture a fingerprint image in a wide area such that many feature points are present.

As described above, by the configuration of the prism according to the present embodiment, a natural image enlarged enough to detect a counterfeit and a fingerprint image in a wide area such that many feature points are present are acquired at the same time, which simultaneously solves the two problems as described earlier.

Moreover, the contrast of the high-contrast image may be enhanced by coating the plane 13 with a black paint or adhesively fixing a blackboard to the plane 13.

Furthermore, mirror coating may be applied to the reflection surface 12 to enhance reflectance.

Moreover, by installing the prism 1 according to the present invention in the conventional contactless living body authentication apparatus, a high-contrast image may be acquired in a similar manner to a contact-type apparatus, and at the same time, a natural image similar to visual observation may be acquired.

Figure 10:
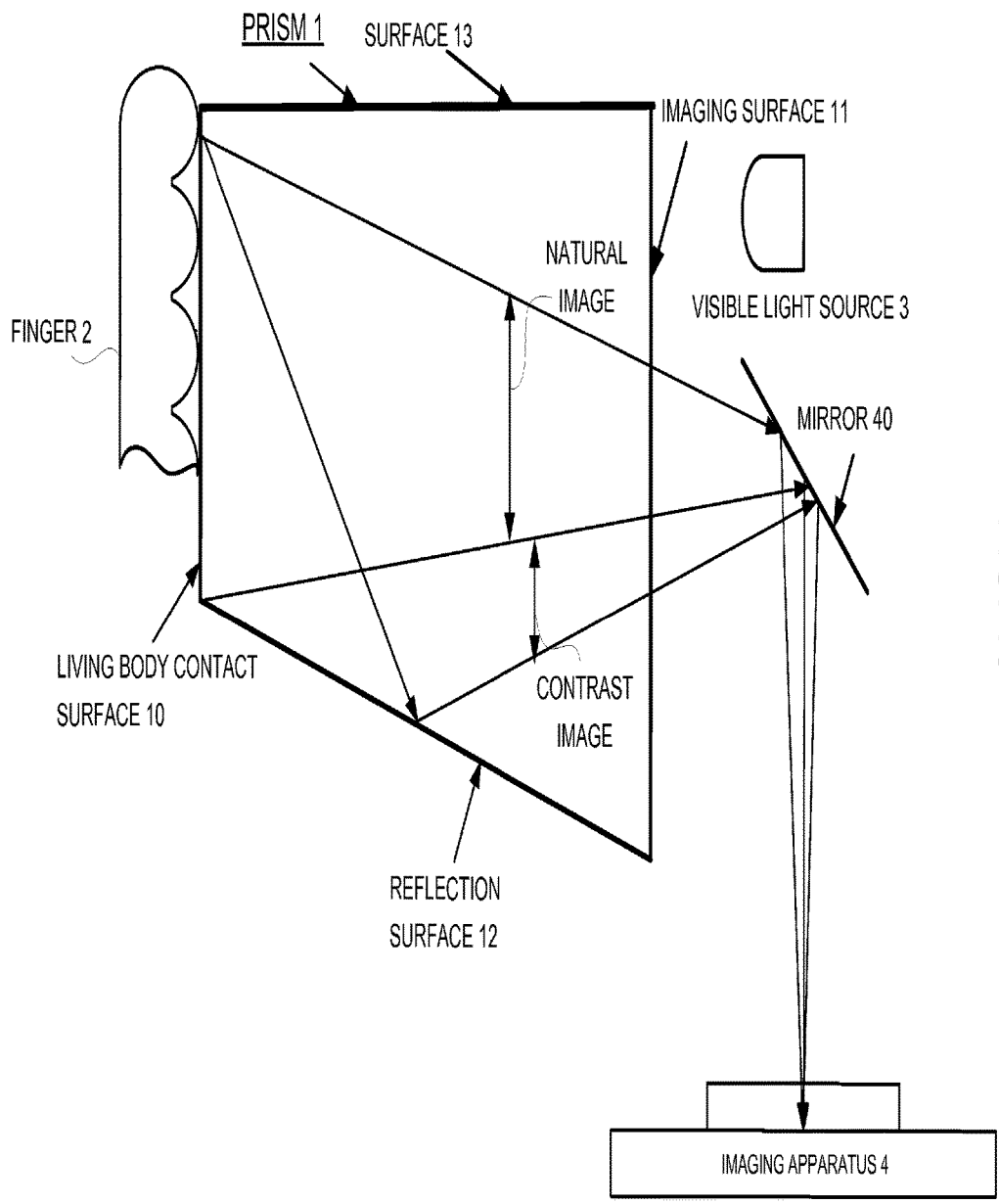
FIG. 10 is a diagram for explaining the prism 1 in accordance with the present invention.

While a case in which the imaging apparatus 4 is disposed below the imaging surface 11 is addressed in the preceding example, the position of the imaging apparatus 4 is not limited to the position below the imaging surface 11. For example, in the case that the authentication apparatus is disposed on a wall, the prism 1 itself is disposed in a position rotated by 90 degrees relative to the preceding example, in which case the imaging apparatus 4 may be disposed at a position to allow imaging on the side of the imaging surface 11 (for example, a position lateral to the imaging surface 11). In addition, as shown in FIG. 10, a mirror 40 may be provided below the imaging surface 11 to reflect light transmitted through the imaging surface 11, and the imaging apparatus 4 may be disposed so that an image reflected on the mirror 40 may be captured. This can reduce the dimension of the authentication apparatus in a depth direction in such a case that the authentication apparatus is installed on a wall.

<First Embodiment>

Now a first embodiment will be described.

Figure 6:
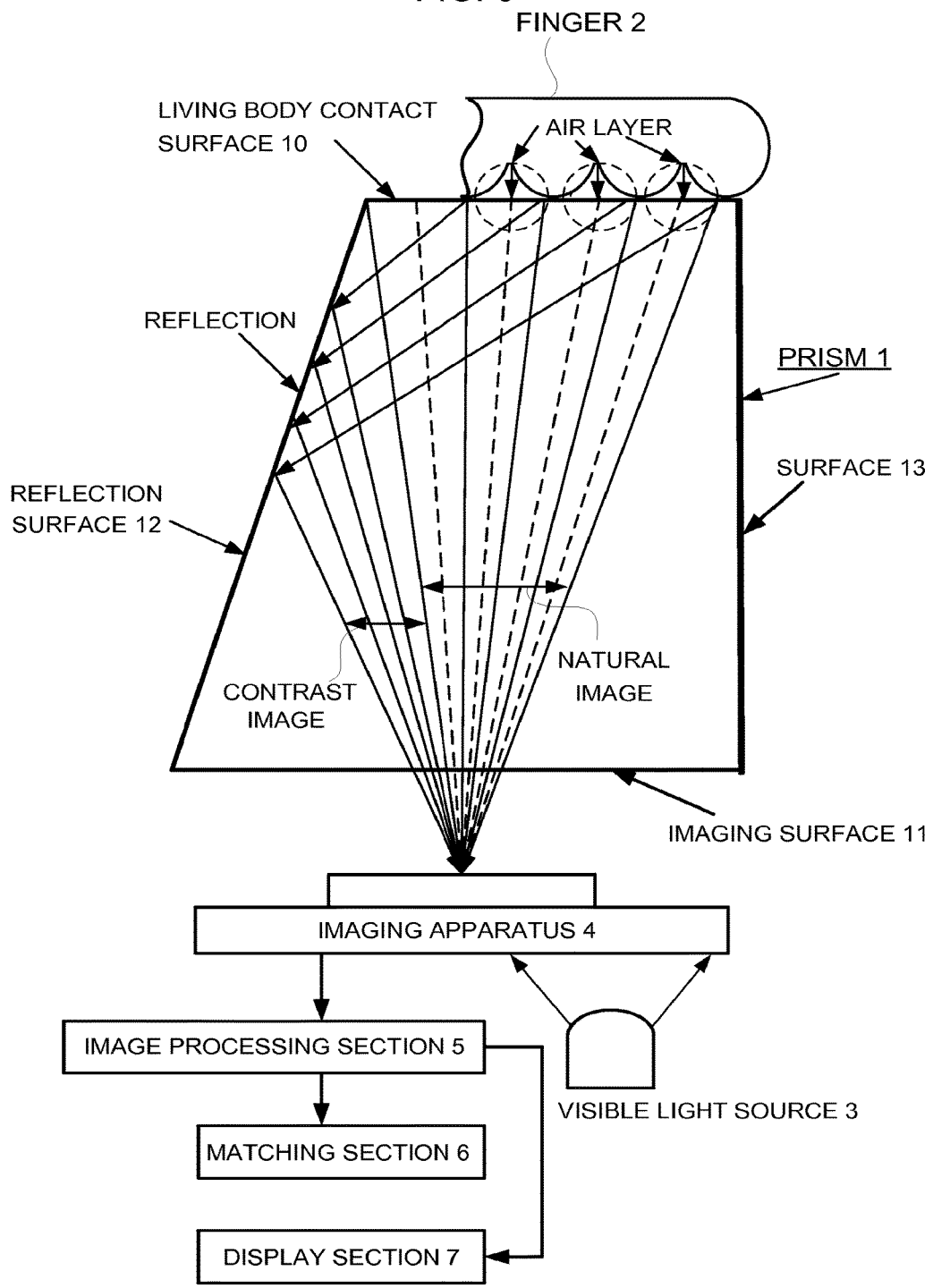
FIG. 6 is a configuration diagram of a fingerprint authentication apparatus in a first embodiment.

FIG. 6 is a configuration diagram of a fingerprint authentication apparatus in the first embodiment.

In the fingerprint authentication apparatus according to the first embodiment, the prism 1 described above is disposed in a position such that the living body contact surface 10 is disposed above the apparatus to serve as a surface against which fingerprints of the finger 2 are put.

Then, the visible light source 3 is disposed below the prism 1. The visible light source 3 may be a white lamp bulb, an LED, and the like.

Moreover, the prism 1 is provided on the side of the imaging surface 11 with the imaging apparatus 4 for capturing via the imaging surface 11 a high-contrast image clearly representing ridges and furrows of fingerprints and a natural image of the fingerprint portion of the fingers. The imaging apparatus 4 is for converting an input image into digital signals and output them, and may employ an image sensor comprised of CCD, CMOS, or the like.

An image processing section 5 converts an image captured by the imaging apparatus 4 into a prespecified image format, and separates the image into a high-contrast image and a natural image, whereupon the high-contrast image is output to a matching section 6 while the natural image is output to the display section 7. The high-contrast image experiences trapezoidal distortion as in a conventional triangular prism, correction of which is applied.

The matching section 6 receives the high-contrast image from the image processing section 5 and applies matching of fingerprints. The fingerprint matching method may be achieved by using any conventional matching method.

The display section 7 receives the natural image from the image processing section 5 and displays it. Thus, criminal acts may be detected, including use of a fake finger fabricated from resin such as silicone, and "identity theft" by attaching a semitransparent bumpy film imitating fingerprints to a real fingertip to pretend to be someone else.

Next, an operation of the living body authentication apparatus described above will be discussed.

First, for authentication, a finger 2 is put against the living body contact surface 10 serving as the surface for putting fingers in the prism 1.

With the fingerprint portion of the finger 2 put against the living body contact surface 10 of the prism 1, the visible light source 3 radiates light to the finger 2 for imaging it.

The light radiated from the visible light source 3 is reflected by furrows and ridges of the finger 2 in contact with the living body contact surface 10.

Since the air has a refractive index of 1.0 while glass has a refractive index of 1.3 to 1.5 and moisture and skin have a refractive index of 1.3 to 1.4, resulting in different refractive indices, a reflected light from the furrows of the finger 2 penetrating into the inside of the prism 1 via the air layer cannot reach the reflection surface 12, so that only a reflected light directly coming from the living body contact surface 10 reaches the imaging surface 11.

On the other hand, a reflected light from the ridges of the finger 2 radiates in all directions in the inside of the prism 1, and travels toward the reflection surface 12 and imaging surface 11. Among these portions of light, some reflected light portions from the ridges traveling toward the reflection surface 12 are totally reflected by the reflection surface 12 and are directed toward the imaging surface 11. Specifically, it is the optical path running from the living body contact surface 10 and reaching the imaging surface 11 by way of the reflection surface 12.

In the imaging apparatus 4, as one of images to be captured, an image for the optical path running from the living body contact surface 10 and reaching the imaging surface 11 by way of the reflection surface 12 is captured. The captured image is a high-contrast image in which the ridges of the finger 2 are highlighted.

Among the reflected light portions reflected by the furrows and ridges of the finger 2 put against the living body contact surface 10, other portions of the light directly reach the imaging surface 11. The reflected light passes through the imaging surface 11 and is captured by the imaging apparatus 4. The image by the reflected light is similar to that by directly observing the finger 2 put against the living body contact surface 10 via the imaging surface 11, and therefore, the image captured by the imaging apparatus 4 is a natural image in which the furrows and ridges of the finger 2 are captured together.

Figure 7:
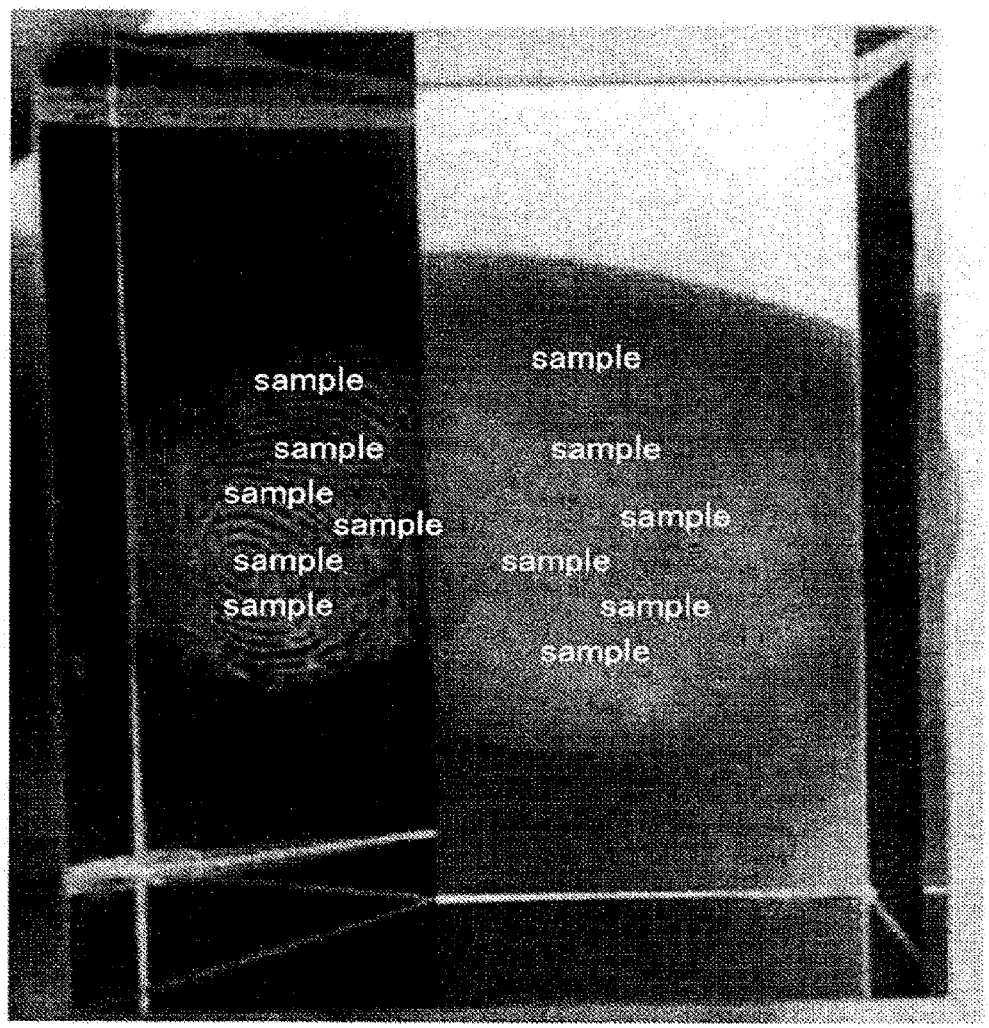
FIG. 7 is a diagram exemplarily showing a high-contrast image and a natural image captured by an imaging apparatus 4.

The imaging apparatus 4 captures the high-contrast image and natural image of the fingerprint portion of the finger 2 by light transmitted through the imaging surface 11 of the prism 1 in one shot of imaging. An exemplary image captured by the imaging apparatus 4 is shown in FIG. 7. As can be seen from FIG. 7, a high-contrast image of the fingerprint portion is captured on the left side of the captured image, and a natural image of the finger 2 including its fingerprint portion is captured on the right side. Of these natural and high-contrast images, the natural image is enlarged as compared with the high-contrast image due to the difference in length of the optical path described above, proving that the natural image enlarged enough to detect a counterfeit can be obtained. On the other hand, it can be seen that the high-contrast image can be obtained as a fingerprint image in a wide area such that many feature points are present.

The image processing section 5 separates the high-contrast image and natural image obtained by the imaging apparatus 4 from each other, and outputs the high-contrast image to the matching section 6 after correcting trapezoidal distortion, and outputs the natural image to the display section 7.

The matching section 6 applies extraction/matching of the feature quantity to the high-contrast image to achieve fingerprint matching and authentication.

The natural image is displayed on the display section 7 to allow decision by visual observation as to whether a fake fingerprint film, tape or the like is used during matching.

Thus, the authentication apparatus according to the first embodiment can provide a natural image similar to visual observation for deciding whether a fake fingerprint film, tape or the like is used and an image with high contrast used for matching fingerprints by one imaging apparatus and in one shot of imaging of fingers. Moreover, a natural image enlarged enough to detect a counterfeit may be obtained.

<Second Embodiment>

A second embodiment will be described.

The second embodiment addresses a case in which, in addition to the configuration of the first embodiment, an infrared light source is provided to capture a blood vessel pattern of fingers by light scattered in the inside of the fingers and transmitted through the fingers.

Figure 8:
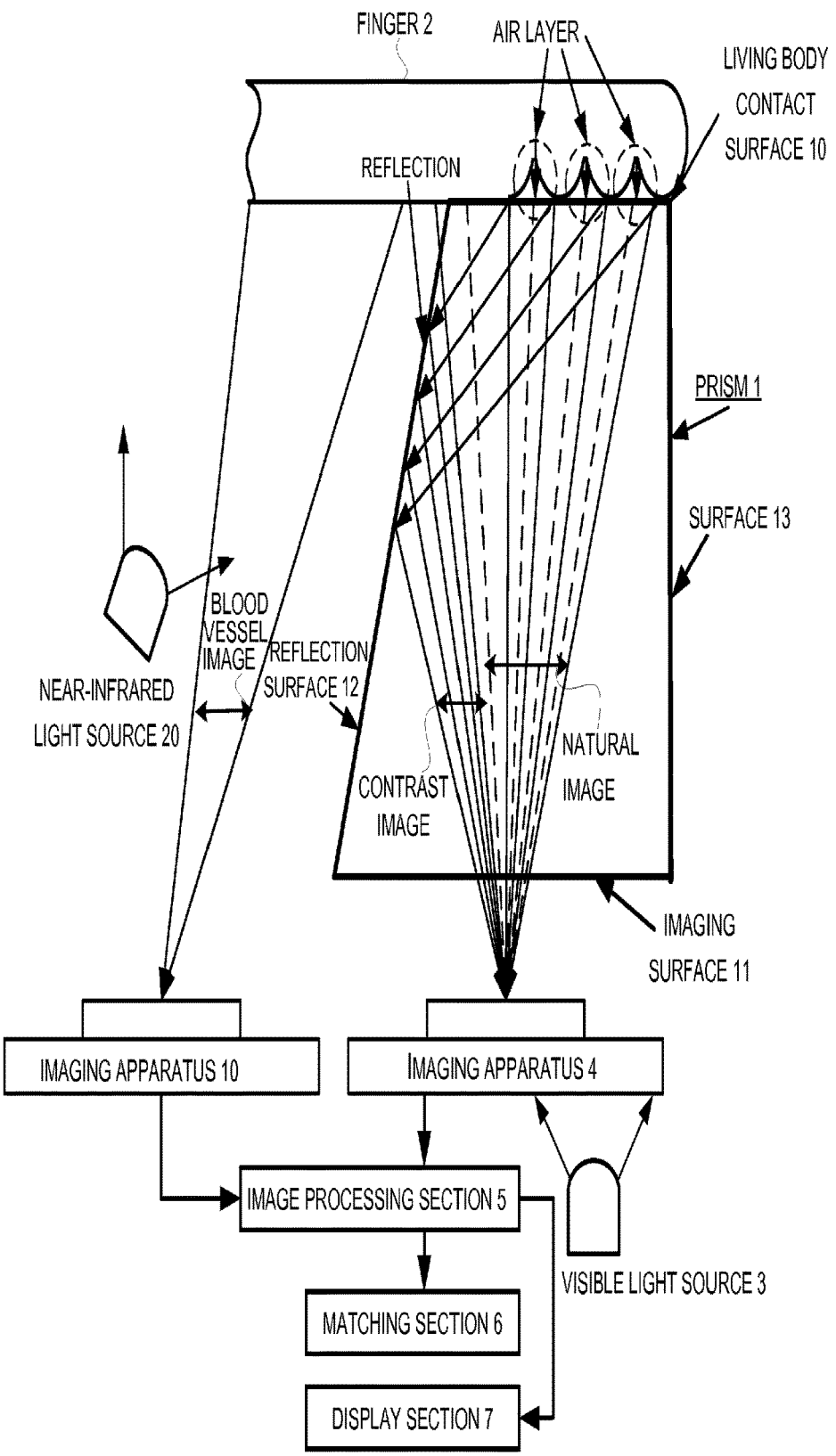
FIG. 8 is a configuration diagram of an authentication apparatus in a second embodiment.

FIG. 8 is a configuration diagram of an authentication apparatus in the second embodiment. As shown in FIG. 8, an infrared light source 20 for an infrared light is added below the finger 2, and an imaging apparatus 21 for blood vessel imaging in which a blood vessel pattern of fingers is captured is provided at a position below the finger 2.

The imaging apparatus 21 is an imaging apparatus including sensitivity to a near-infrared light, and captures a near-infrared image of blood vessels in the fingers with a wavelength ranging from 700 to 1000 nm in which oxyhemoglobin in blood is favorably absorbed and sensitivity to biological pigments is low.

In the second embodiment, the visible light source 3 that is a white light source and the infrared light source 20 for an infrared light are temporally switched for imaging. For example, the visible light source 3 that is a white light source is first activated to radiate light, and a natural image and a high-contrast image are captured by the imaging apparatus 4. Next, an infrared light source 20 for an infrared light is activated to radiate light, and a blood vessel pattern of fingers is captured by the imaging apparatus 21. These operations may be performed in a reverse order.

According to the second embodiment, in addition to the effects in the first embodiment, variation of an image due to blood-flow-induced pulsation and subcutaneous tissue may be observed for use in living body identification to achieve living body identification with higher precision.

<Third Embodiment>

A third embodiment will be described.

The third embodiment addresses a case in which, in addition to the configuration of the first embodiment, an infrared light source 20 for an infrared light is provided to simultaneously capture a blood vessel pattern of fingers by an infrared light, and a high-contrast image and a natural image.

Figure 9:
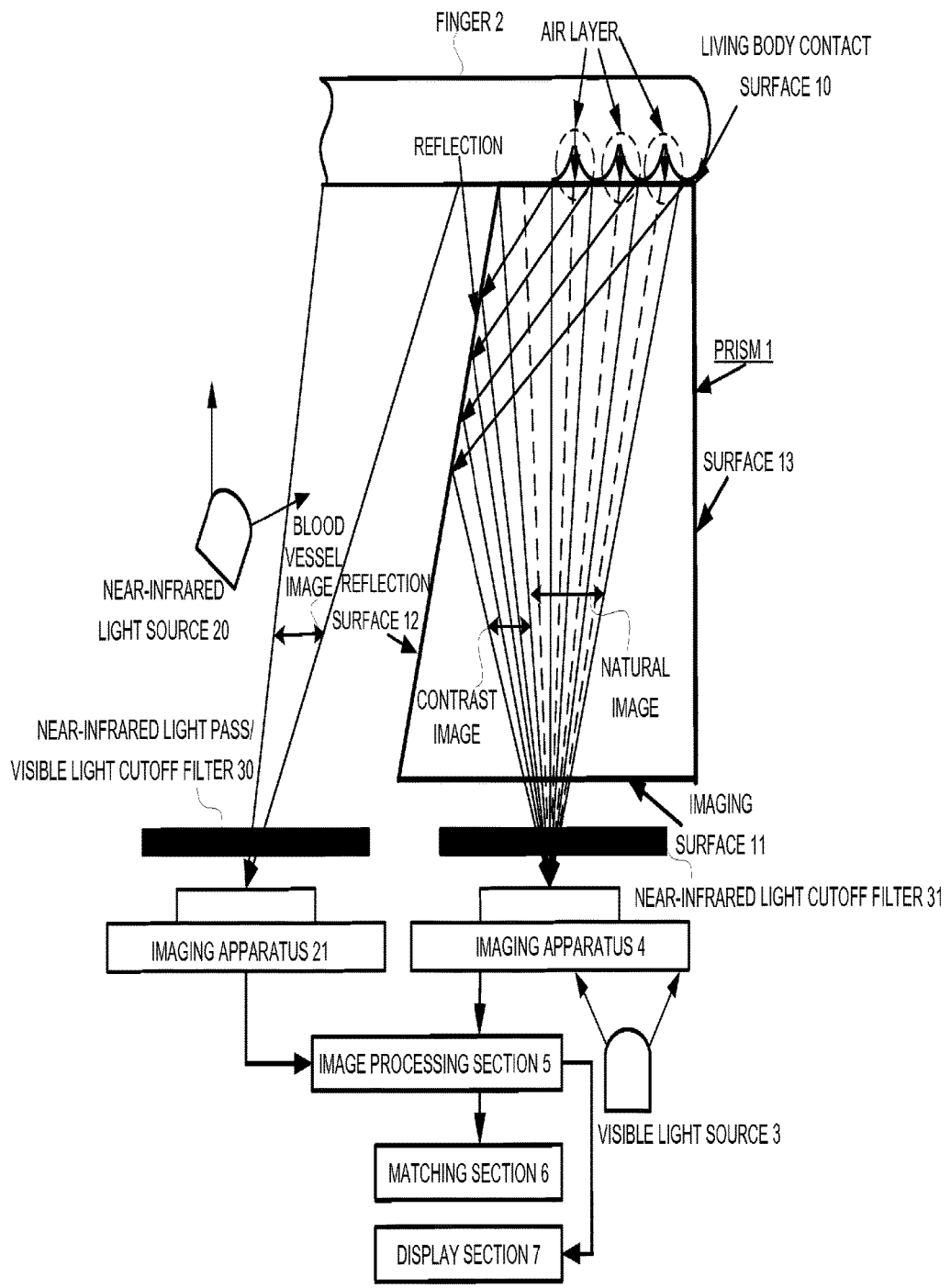
FIG. 9 is a configuration diagram of an authentication apparatus in a third embodiment.

FIG. 9 is a configuration diagram of an authentication apparatus in the third embodiment. As shown in FIG. 9, an infrared light source 20 for an infrared light is added below the finger 2, and an imaging apparatus 21 for blood vessel imaging in which a blood vessel pattern of fingers is captured is provided at a position below the finger 2. A difference from the second embodiment is in that a visible light cutoff/infrared light pass filter 30 for cutting off a visible light portion of an incident light and passing an infrared light is provided between the lower portion of the finger 2 and imaging apparatus 21. Thus, a visible light is cut off and only an infrared light is introduced into the imaging apparatus 21. Moreover, an infrared light cutoff filter 31 for cutting off an infrared light portion of an incident light and passing a visible light is provided between the imaging surface 11 and imaging apparatus 4. Thus, only a visible light with an infrared light cut off is introduced into the imaging apparatus 4.

According to the configuration described above, the visible light source 3 that is a source of a visible light and the infrared light source 20 that is a source of an infrared light may be simultaneously activated to radiate light, whereby capture of a natural image and a high-contrast image by the imaging apparatus 4 and imaging of a blood vessel pattern of fingers by the imaging apparatus 21 may be simultaneously achieved, so that a natural image and a high-contrast image, as well as an image of a blood vessel pattern of fingers may be simultaneously obtained in one shot of imaging.

Moreover, the infrared light cutoff filter 31 provided below the finger 2 can prevent foreign materials such as dust and dirt from entering the inside of the authentication apparatus, which also facilitates maintenance of the authentication apparatus.

As is obvious from the preceding description, while several parts may be configured in hardware, they also may be implemented by a computer program. In this case, a processor that is operated by programs stored in a program memory implements functions and/or operations similar to those in the embodiments described above. Moreover, only part of functions of the embodiments described above may be implemented by a computer program.

Furthermore, part or all of the preceding embodiments may be described as in the following appendices, although not limited thereto.

(Supplementary Note 1) An authentication apparatus including a prism member, a first imaging unit, and a visible light source configured to radiate a visible light to a living body,
wherein said prism member comprises:
a living body contact surface configured to be in contact with the living body;
an imaging surface configured to be opposed to said living body contact surface and be formed at a position in generally parallel therewith; and
a reflection surface configured to be in contact with said living body contact surface and said imaging surface, and to totally reflect light reflected off from said living body contact surface toward said imaging surface,
wherein said reflection surface is disposed at such an angle that light from an inside of said prism member is totally reflected at said living body contact surface in an optical path running from said imaging surface and reaching said living body contact surface by way of said reflection surface, and
said first imaging unit captures a living-body reflected light that is light radiated from said visible light source reflected off by the living body in contact with said living body contact surface, and a reflection surface reflected light that is said living-body reflected light reflected off by said reflection surface.

(Supplementary Note 2) The authentication apparatus according to supplementary note 1, wherein:
said prism member comprises an opposite surface configured to be in generally perpendicular contact with said living body contact surface and said imaging surface, and to be formed at a position opposite to said reflection surface, and
at least part of said opposite surface is coated with black or attached with a blackboard.

(Supplementary Note 3) The authentication apparatus according to supplementary note 1 or 2, wherein:
mirror coating is applied to said reflection surface.

(Supplementary Note 4) The authentication apparatus according to any one of supplementary notes 1 to 3, comprising:
an infrared light source configured to radiate an infrared light to said living body; and
a second imaging unit configured to capture an infrared light transmitted through said living body.

(Supplementary Note 5) The authentication apparatus according to supplementary note 4, wherein:
a visible light pass filter configured to cut off an infrared light is disposed in front of said first imaging unit, and
an infrared light pass filter configured to cut off a visible light is disposed in front of said second imaging unit.

(Supplementary Note 6) The authentication apparatus according to any one of supplementary notes 1 to 5, wherein:
an image obtained by imaging said living-body reflected light is a natural image for detecting a counterfeit, and
an image obtained by imaging said reflection surface reflected light is a contrast image for authentication of a living body.

(Supplementary Note 7) The authentication apparatus according to any one of supplementary notes 1 to 6, wherein:
said living body is a human finger.

(Supplementary Note 8) A prism member for authentication of a living body, comprising:
a living body contact surface configured to be in contact with a living body;
an imaging surface configured to be opposed to said living body contact surface and be formed at a position in generally parallel therewith; and
a reflection surface configured to be in contact with said living body contact surface and said imaging surface, and to totally reflect light reflected off from said living body contact surface toward said imaging surface,
wherein said reflection surface is disposed at such an angle that light from an inside of said prism member is totally reflected at said living body contact surface in an optical path running from said imaging surface and reaching said living body contact surface by way of said reflection surface.

(Supplementary Note 9) The prism member for authentication of a living body according to supplementary note 8, wherein:
said prism member comprises an opposite surface configured to be in generally perpendicular contact with said living body contact surface and said imaging surface, and to be formed at a position opposite to said reflection surface, and
at least part of said opposite surface is coated with black or attached with a blackboard.

(Supplementary Note 10) The prism member for authentication of a living body according to supplementary note 8 or 9, wherein:

mirror coating is applied to said reflection surface.

(Supplementary Note 11) An authentication method, in a prism member comprising:

a living body contact surface configured to be in contact with a living body;

an imaging surface configured to be opposed to said living body contact surface and be formed at a position in generally parallel therewith; and a reflection surface configured to be in contact with said living body contact surface and said imaging surface, and to totally reflect light reflected off from said living body contact surface toward said imaging surface, wherein said reflection surface is disposed at such an angle that light from an inside of said prism member is totally reflected at said living body contact surface in an optical path running from said imaging surface and reaching said living body contact surface by way of said reflection surface, said method comprising:

bringing a living body into contact with said living body contact surface of said prism member;

radiating a visible light to said living body; and imaging a living-body reflected light that is light radiated from said visible light source and transmitted through said imaging surface reflected off by the living body in contact with said living body contact surface, and a reflection surface reflected light that is said living-body reflected light reflected off by said reflection surface.

(Supplementary Note 12) The authentication method according to supplementary note 11, wherein:

said prism member comprises an opposite surface configured to be in generally perpendicular contact with said living body contact surface and said imaging surface, and to be formed at a position opposite to said reflection surface, and at least part of said opposite surface is coated with black or attached with a blackboard.

(Supplementary Note 13) The authentication method according to supplementary note 11 or 12, wherein:

mirror coating is applied to said reflection surface.

(Supplementary Note 14) The authentication method according to any one of supplementary notes 11 through 13, comprising:

radiating an infrared light to said living body; and imaging an infrared light transmitted through said living body.

(Supplementary Note 15) The authentication method according to supplementary note 14, wherein:

said living-body reflected light and said reflection surface reflected light are captured by an imaging apparatus provided with a visible light pass filter configured to cut off an infrared light; and said infrared light is captured by an imaging apparatus provided with an infrared light pass filter configured to cut off a visible light.

(Supplementary Note 16) The authentication method according to any one of supplementary notes 11 through 15, wherein:

an image obtained by capturing said living-body reflected light is a natural image for detecting a counterfeit, and an image obtained by capturing said reflection surface reflected light is a contrast image for authentication of a living body.

(Supplementary Note 17) The authentication method according to any one of supplementary notes 11 through 16, comprising:

correcting trapezoidal distortion in said obtained contrast image by means of image processing.

(Supplementary Note 18) The authentication method according to any one of supplementary notes 11 through 17, wherein:

said living body is a human finger.

While the present invention has been described with reference to the preferred embodiments, it is not necessarily limited to the embodiments described above, and may be practiced with several modifications within a scope of the technical idea thereof.

The present application claims priority based on Japanese Patent Application No. 2013-016746 filed on Jan. 31, 2013, disclosure of which is incorporated herein in its entirety.

REFERENCE SIGNS LIST

1 Prism
2 Finger
3 Visible light source
4 Imaging apparatus
5 Image processing section
6 Matching section
7 Display section
10 Living body contact surface
11 Imaging surface
12 Reflection surface
13 Surface
20 Infrared light source
21 Imaging apparatus
30 Visible light cutoff/infrared light pass filter
31 Infrared light cutoff filter
40 Mirror

The invention claimed is:

1. An authentication apparatus including:

a prism member;

a first imaging unit; and a visible light source configured to radiate a visible light to a living body, wherein the prism member comprises:

a living body contact surface configured to be in contact with the living body;

an imaging surface configured to be opposed to the living body contact surface and to be formed at a position generally parallel therewith; and a reflection surface configured to be in contact with the living body contact surface and the imaging surface, and to totally reflect light reflected off from the living body contact surface toward the imaging surface, wherein the reflection surface is disposed at such an angle that first light that is radiated from the light source, then transmitted through the imaging surface, then reflected by the living body, then passes through the living body contact surface into the prism member to the imaging surface without reaching to the reflection surface, wherein the reflection surface is disposed at such an angle that second light that is transmitted from the visible light source, through the imaging surface, then passes inside of the prism member, is then totally reflected at the living body contact surface, is then reflected by the reflection surface, and then passes to the imaging surface, and wherein the first imaging unit is configured to capture, via the imaging surface, an image including at least a part of the living body contact surface by using the first light and at least a part of the reflection surface by using the second light.

2. The authentication apparatus according to claim 1, wherein the prism member comprises an opposite surface configured to be generally in perpendicular contact with the living body contact surface and the imaging surface, and to be formed at a position opposite to the reflection surface, and
wherein at least part of the opposite surface is coated with black or attached to a blackboard.

3. The authentication apparatus according to claim 1, wherein mirror coating is applied to the reflection surface.

4. The authentication apparatus according to claim 1, wherein the first imaging unit is configured to acquire a natural image of the living body using the first light, and
wherein the first imaging unit is configured to acquire a contrast image using the second light.

5. The authentication apparatus according to claim 4, wherein the first imaging unit is configured to simultaneously acquire the natural image and the contrast image.

6. An authentication method comprising:
bringing a living body into contact with a living body contact surface of a prism member of an authentication apparatus,
wherein the authentication apparatus comprises the prism member, a first imaging unit, and a visible light source,
wherein the prism member comprises:
a living body contact surface configured to be in contact with the living body;
an imaging surface configured to be opposed to the living body contact surface and to be formed at a position generally parallel therewith; and
a reflection surface configured to be in contact with the living body contact surface and the imaging surface, and to total reflect light reflected from the living body contact surface toward the imaging surface,
wherein the reflection surface is disposed at such an angle that light from an inside of the prism member is totally reflected at the living body contact surface;
radiating a visible light, from the visible light source, to the living body;
capturing an image via the imaging surface;
separating the captured image into a first part and a second part,
wherein the first part of the captured image includes at least a part of the body contact surface, and
wherein the second part of the captured image includes at least a part of the reflection surface;
outputting the first part of the captured image to a display device; and
applying matching of fingerprints using the second part of the captured image.

7. The authentication method according to claim 6, wherein the prism member comprises an opposite surface configured to be generally in perpendicular contact with the living body contact surface and the imaging surface, and to be formed at a position opposite to the reflection surface, and
wherein at least part of the opposite surface is coated with black or attached to a blackboard.

8. The authentication method according to claim 6, wherein mirror coating is applied to the reflection surface.

9. The authentication method according to claim 6, wherein the first part of the captured image is obtained using first light that is radiated from the visible light source, then transmitted through the imaging surface, then reflected by the living body, and then passes through the living body contact surface into the prism member to the imaging surface without reaching to the reflection surface.

10. The authentication method according to claim 6, wherein the second part of the captured image is obtained using second light that is transmitted from the visible light source, through the imaging surface, then passes inside the prism member, is then totally reflected at the living body contact surface, is then reflected by the reflection surface, and then passes to the imaging surface.

11. A non-transitory computer-readable recording medium storing a program that, when executed, causes a computer to execute an authentication method comprising:
bringing a living body into contact with a living body contact surface of a prism member of an authentication apparatus,
wherein the authentication apparatus comprises the prism member, a first imaging unit, and a visible light source,
wherein the prism member comprises:
a living body contact surface configured to be in contact with the living body;
an imaging surface configured to be opposed to the living body contact surface and to be formed at a position generally parallel therewith; and
a reflection surface configured to be in contact with the living body contact surface and the imaging surface, and to totally reflect light reflected from the living body contact surface toward the imaging surface,
wherein the reflection surface is disposed at such an angle that light from an inside of the prism member is totally reflected at the living contact surface;
radiating a visible light, from the visible light source, to the living body;
capturing an image via the imaging surface;
separating the captured image into a first part and a second part,
wherein the first part of the captured image includes at least a part of the body contact surface, and
wherein the second part of the captured image includes at least a part of the reflection surface;
outputting the first part of the captured image to a display device; and
applying matching of fingerprints using the second part of the captured image.

12. The non-transitory computer-readable recording medium according to claim 11, wherein the prism member comprises an opposite surface configured to be generally in perpendicular contact with the living body contact surface and the imaging surface, and to be formed at a position opposite to the reflection surface, and
wherein at least part of the opposite surface is coated with black or attached to a blackboard.

13. The non-transitory computer-readable recording medium according to claim 11, wherein mirror coating is applied to the reflection surface.

14. The non-transitory computer-readable recording medium according to claim 11, wherein the first part of the captured image is obtained using first light that is radiated from the visible light source, then transmitted through the imaging surface, then reflected by the living body, and then passes through the living body contact surface into the prism member to the imaging surface without reaching to the reflection surface.

15. The non-transitory computer-readable recording medium according to claim 11, wherein the second part of the captured image is obtained using second light that is transmitted from the visible light source, through the imaging surface, then passes inside the prism member, is then totally reflected at the living body contact surface, is then reflected by the reflection surface, and then passes to the imaging surface.

* * * * *